(12) United States Patent
Mölter et al.

(10) Patent No.: US 7,543,803 B2
(45) Date of Patent: Jun. 9, 2009

(54) METHOD AND APPARATUS FOR HUMIDIFYING GAS AND FOR CONDENSING STEAM ON CONDENSATION NUCLEI

(75) Inventors: Leander Mölter, Wörth (DE); Friedrich Munzinger, Gondelsheim (DE)

(73) Assignee: Palas GmbH Partikel- und Lasermesstechnik, Karlsruhe (DE)

( * ) Notice: Subject to any disclaimer, the term of this patent is extended or adjusted under 35 U.S.C. 154(b) by 492 days.

(21) Appl. No.: 11/332,209

(22) Filed: Jan. 17, 2006

(65) Prior Publication Data

US 2006/0158640 A1    Jul. 20, 2006

(30) Foreign Application Priority Data

Jan. 15, 2005    (DE) .................... 10 2005 001 992

(51) Int. Cl.
   *B01F 3/04*    (2006.01)
(52) U.S. Cl. .................. 261/135; 261/147; 261/153
(58) Field of Classification Search ............... 261/135, 261/147, 153, 79.2, 110, 112.1, DIG. 10
   See application file for complete search history.

(56) References Cited

U.S. PATENT DOCUMENTS

| | | | | | |
|---|---|---|---|---|---|
| 2,817,415 | A | * | 12/1957 | Sykes | .................... 95/219 |
| 3,733,786 | A | * | 5/1973 | Koka | .................... 96/314 |
| 3,738,751 | A | | 6/1973 | Rich | |
| 3,854,468 | A | * | 12/1974 | Nozaki | .................... 126/113 |
| 4,038,347 | A | * | 7/1977 | Mickley | .................... 261/30 |
| 4,051,205 | A | | 9/1977 | Grant | |
| 4,059,419 | A | * | 11/1977 | Ross | .................... 95/214 |
| 4,060,576 | A | | 11/1977 | Grant | |
| 5,366,667 | A | * | 11/1994 | Le Goff | .................... 261/153 |
| 5,903,338 | A | | 5/1999 | Mavliev | |

FOREIGN PATENT DOCUMENTS

| | | |
|---|---|---|
| DE | 23 45 677 | 3/1974 |
| WO | WO89/08245 | 9/1989 |
| WO | WO02/29382 | 4/2002 |

* cited by examiner

*Primary Examiner*—Scott Bushey
(74) *Attorney, Agent, or Firm*—Antonelli, Terry, Stout & Kraus, LLP.

(57) ABSTRACT

For the reliable condensation of steam on condensation nuclei in an aerosol flow and therefore for enlarging the particles in the aerosol, the invention provides a method which is characterized in that condensation nuclei are passed through an inner area of an evaporating zone forming a flow area, the liquid to be evaporated is contacted with the flow area and evaporated therein and the thus produced steam is condensed on the condensation nuclei. the invention also provides an apparatus for condensing steam on condensation nuclei with an inlet for condensation nuclei and an evaporating zone constructed in such a way that a flow area for the condensation nuclei has a heated liquid duct open thereto and that a condensation flue is connected to the flow area. The invention also provides methods and apparatuses for counting particles, for producing monodisperse aerosols using the aforementioned method or the aforementioned apparatus.

29 Claims, 6 Drawing Sheets

Fig. 6

METHOD AND APPARATUS FOR HUMIDIFYING GAS AND FOR CONDENSING STEAM ON CONDENSATION NUCLEI

FIELD OF THE INVENTION

The invention relates to methods and apparatuses for humidifying gas, in particular air, and for condensing steam on condensation nuclei, the latter having an inlet for condensation nuclei and an evaporation zone for a liquid.

BACKGROUND OF THE INVENTION

In many gaseous carriers, such as air, exhaust gases or the like, there are particles having a smaller size than can be directly and immediately detected by conventional detection means, such as particle counters or aerosol spectrometers. However, the detection of such particles is important, because they can have a considerable influence, e.g. in the respiratory air on the health, effectiveness and service life of filters. To enable such particles to be detected, they are "enlarged" by condensing on steam and they then function as condensation nuclei.

There is normally a storage vessel with a substance to be evaporated. The substance is brought into a humidifier means with the aid of a porous material such as felt and the like and in the same the substance evaporates. The aerosol to be measured is then passed with the steam into a condensing tube and the steam condenses on the aerosol particles and enlarges the latter. It is possible to work with external cooling and optionally also with aerosol injection or with a turbulent mixture. The apparatus and therefore also the method are sensitive for "enlargement".

In addition, optical aerosol spectrometers are calibrated, preferably by monodisperse droplets in the range 0.2 to 8 μm. Use is made of a Sinclair-LaMer generator for producing such droplets or particles. Initially very small particles with a diameter smaller than 100 nanometers are generated as condensation nuclei and are passed through a heated, saturated steam atmosphere. Said steam-particle mixture is then passed through a cooled condensing tube in which the steam substance condenses on the nucleus. These method apparatuses are very complicated and also fault-prone, particularly if specific, precise particle sizes are required.

The problem of the invention is to provide methods and apparatus for humidifying gas, particularly air, and for condensing steam on condensation nuclei, which are simple, reliable and insensitive.

SUMMARY OF THE INVENTION

According to the invention the set problem is solved by a method of the aforementioned type and which is characterized in that the gas is passed through the inner area of an evaporation zone forming a flow area, the liquid to be evaporated is brought into contact with the flow area and evaporated therein.

For solving the set problem the invention also provides a device for humidifying gas of the aforementioned type and which is characterized in that a flow area has a heated liquid duct open thereto.

For solving the second partial problem the invention provides a method for condensing steam on condensation nuclei, in which the gas is humidified in the above-described manner, condensation nuclei being passed with the gas through the flow area and the steam produced is condensed on the condensation nuclei.

An inventive apparatus for condensing steam on condensation nuclei is characterized by a device for humidifying gas constructed in the manner described hereinbefore and by a condensation flue connected to the flow area.

The invention leads to a number of advantages compared with the prior art and permanent operation lasting several months is possible. It is possible to use the most varied substance materials such as water, alcohols, oils or the like. An automatic activation and deactivation of the supply of liquid to be evaporated is possible, as is a simple, rapid steam quantity control. The device according to the invention can be easily cleaned. The device according to the invention can also be constructed as a closed system, there being independence of the ambient pressure and the device according to the invention is usable in the case of overpressure and underpressure and the method can be correspondingly performed.

According to a preferred development of the method the gas and also the condensation nuclei are moved from top to bottom with at least one component of motion through the evaporation zone and a following condensation flue and in particular the gas and also the condensation nuclei are moved through the substantially vertically oriented evaporation zone and optionally the condensation flue. To this end the inventive device provides that there is an inlet for the gas in the flow area on the top of the latter. In particular, the flow area and optionally the condensation flue is vertically oriented and the former is positioned above the latter.

This development creates the prerequisite that the particles enlarged by condensing on, the starting size being in the nano-range, e.g. smaller than 100 nm, can move by gravity through the evaporation zone and through an aerosol spectrometer.

Thus, according to a further preferred development of the inventive method, the liquid to be evaporated is moved helically around the flow area and for this purpose the inventive device is constructed in such a way that the liquid duct is placed as a helical channel around the flow area. In this connection the inlet for the liquid to be evaporated is placed in the evaporation zone above the outlet for liquid not evaporated in said evaporation zone.

As a result of a helical construction of the duct guiding the liquid to be evaporated the path of the liquid in the evaporation zone is maximized and the flow rates reduced, so that there is a long residence time of the liquid to be evaporated in the evaporation zone.

In further preferred developments of the invention, the liquid to be evaporated is delivered from a storage container by means of a pump to the flow area and the apparatus is constructed in such a way that the liquid inlet in the liquid duct is positioned above the outlet for unevaporated residual liquid and in particular a liquid container and a pump are positioned upstream of the inlet for liquid to be evaporated in the flow area.

This leads to a continuous circulation of the substance to be evaporated. In a preferred, specific development of the inventive device, the liquid to be evaporated is fed to the inlet of the helical channel and the liquid then slowly flows downwards in the channel and is evaporated by a heater. Unevaporated substance can be returned to a storage container. Therefore the pump can deliver more liquid than would be required for a 100% saturation. The storage container is firmly connected, so that the aforementioned closed circuit is formed. By a corresponding temperature setting, an overpressure and underpressure measurement are possible.

Essential advantages of the apparatus according to the invention are free passage, a very good thorough mixing, adjustable steam quantity by temperature and delivery (pump), return of the excess substance and tightly sealed storage container. In addition, the steam quantity is not dependent on the steam pressure, because through superheating and delivery by a pump supersaturation can be achieved. The liquid flow can be easily adjusted, so that the steam quantity can be rapidly modified. The nature of the liquid, such as in particular isopropanol, butanol, etc., cannot be changed by the user.

The method and apparatus according to the invention for condensing steam on condensation nuclei offer numerous possible uses. Thus, the invention also provides a method for counting particles, in which steam initially condenses on condensation nuclei-forming particles in accordance with the inventive method and then the condensation nuclei provided with the condensation steam are counted. To this end an apparatus for counting particles with a particle counter, optionally as an aerosol spectrometer forming the same, is constructed in such a way that upstream of the particle counter is provided an inventive apparatus for condensing steam on condensation nuclei.

Within the scope of the invention is also provided a method for producing monodisperse aerosol, in which condensation nuclei of a predetermined, defined concentration are produced and steam is condensed thereon in accordance with the inventive method for condensing steam on condensation nuclei. A corresponding apparatus for producing a monodisperse aerosol involves the aerosol generator being followed by at least one inventive apparatus for condensing steam on condensation nuclei. In this development the method and apparatus according to the invention offer the advantages that a rapid particle size adjustment is possible without a bypass around a saturator, because the particle size is directly controlled the steam quantity, which can be rapidly controlled in a direct manner through the pump delivery. The manufacture and handling of the apparatus and the method according to the invention are simple, no reheater being necessary.

In a preferred development of the method according to the invention steam for condensing on condensation nuclei can be repeatedly produced in series, particularly twice and an inventive apparatus is constructed in such a way that several and preferably two inventive apparatuses are successively arranged in series for condensing steam on condensation nuclei. Through the cascading of evaporation units it is possible to produce larger particles by the multiple attachment of steam by condensation on particles. It is thus possible to produce particles from different materials, in that in two or more successive evaporation units use is made of different liquids to be evaporated. As a result of the cascading of the evaporating units particles from different materials can be produced. The inventive method allows a 100% saturation of the steam in each further evaporating unit, because the carrier gas volume flow remains the same.

In a highly advantageous manner the invention also provides a method for counting small diameter particles, which is characterized in that the particles are counted in a gas flow, subsequently steam is condensed on the particles forming the condensation nuclei and in particular according to the inventive method for condensing steam on condensation nuclei, the condensate provided with the condensate particles being counted therewith following the condensation of steam and the difference between the particle quantities counted before and after condensation is formed, so as in this way to permit the determination of the particles in the inflowing aerosol below a measurable limit. In this connection the invention also provides an apparatus for counting small diameter particles with two particle counters, optionally in the form of aerosol spectrometers and which is characterized in that a first particle counter is followed by an inventive apparatus for condensing steam on condensation nuclei and the latter is in turn followed by a further particle counter. Through the subtraction of the counted particles before and after condensation it is also possible to determine the number of very small particles, whose size as such is below the normal detection limit. Provided that use is made of an aerosol spectrometer at least as the first counter in the flow, the distribution of the larger diameter particles can also be established.

BRIEF DESCRIPTION OF THE DRAWINGS

Further advantages and features of the invention can be gathered from the claims and the following description of embodiments of the invention with reference to the attached drawings, wherein show:

DETAILED DESCRIPTION OF THE DRAWINGS

The inventive device 1 for humidifying steam (FIG. 1) has an evaporating zone 3 connecting onto an inlet 2.

Figure 1:
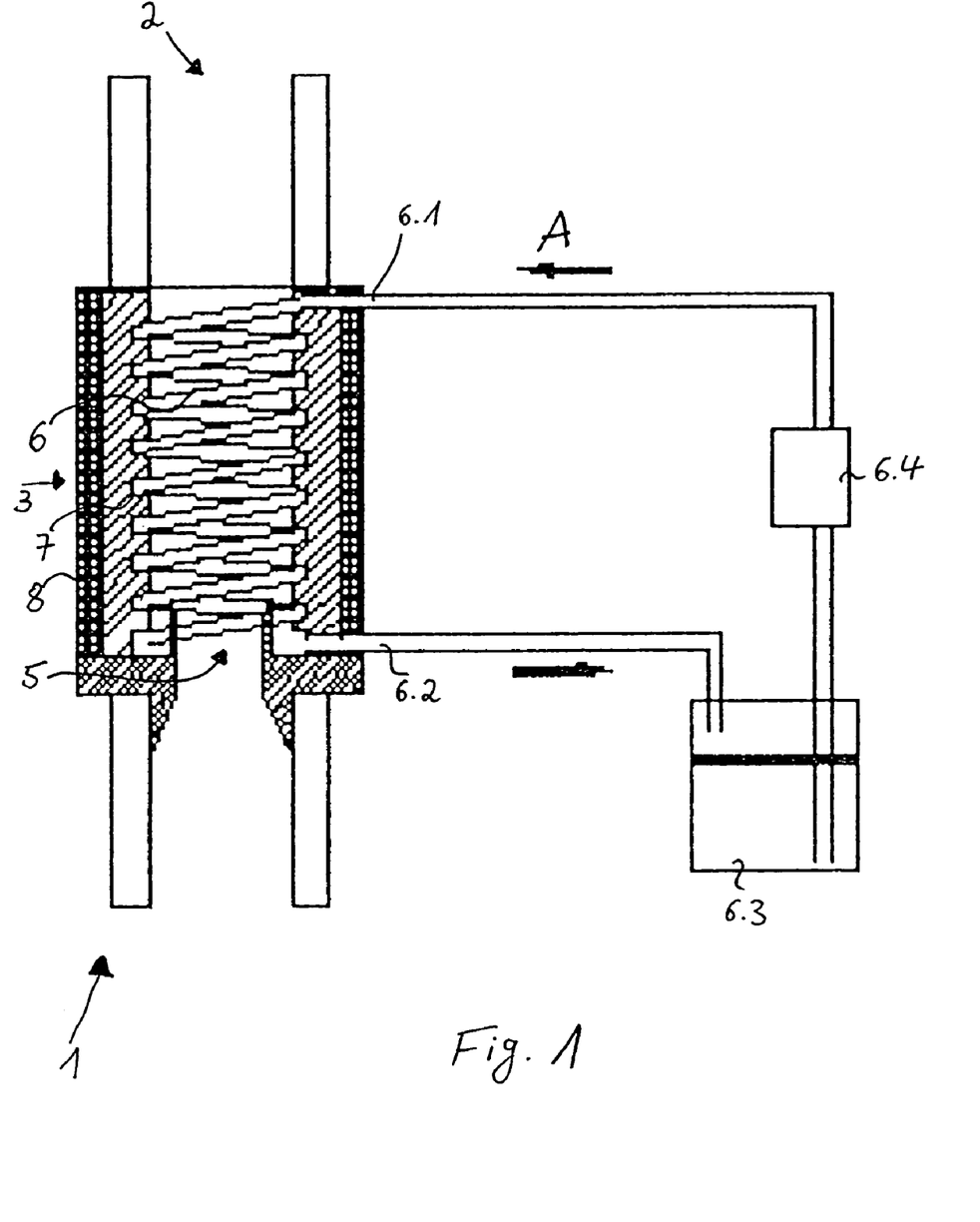
FIG. 1 An inventive apparatus as an air humidifier with a free passage.

The evaporating zone 3 has an elongated, tubular passage 5 forming a flow area and which is in particular cylindrical with a circular cross-section, but can also have a different contour, e.g. elliptical, oval, square or rectangular cross-section.

A duct 6 passes round the passage 5 and is open thereto, in the embodiment shown said duct being helical and is formed in the wall 7 of passage 5, here in the form of a cylinder jacket wall. The duct 6 is not porous and is in particular smooth. The duct 6 is heated and in the embodiment shown the wall 7 is surrounded by a heater 8 in the form of a cylinder jacket and engaging closely with the wall 7. The wall 7 is made from a good heat conducting material such as metal. The heater can be constructed in the conventional manner, e.g. using resistance wires, hot or cold conductors in wire or ceramic form. Electrical contact between the wall 7 and heating elements, such as heating wires, is prevented by a not shown insulating layer.

Figure 2A:
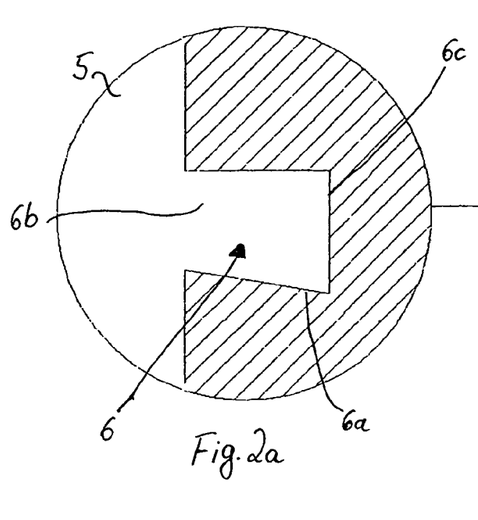
FIGS. 2a & 2b On a larger scale cross-sectional shapes of evaporation liquid-carrying ducts at A in FIG. 3.
Figure 2B:
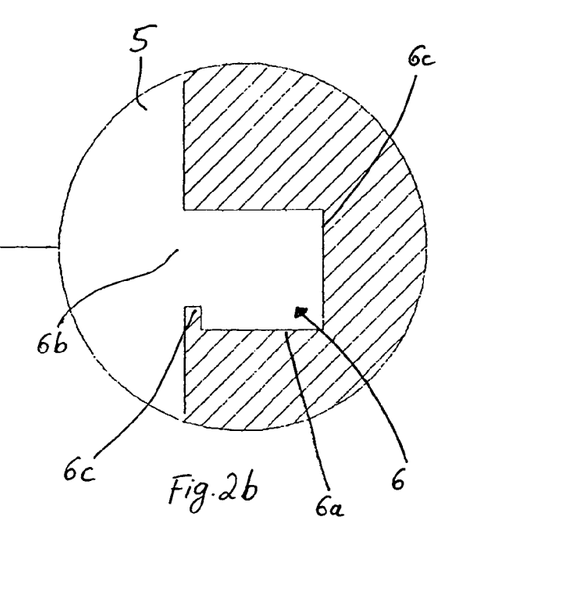

The duct 6 is preferably constructed as an open channel. Its bottom 6a can be inclined and passes from its side 6b open towards the flow area 5 downwards to its wall 6c remote from said flow area (FIG. 2a). Alternatively on the side 6b facing the flow area can be formed as from the bottom a high wall 6d only representing part of the duct height (FIG. 2b). The duct 6 by means of an inlet 6.1 and an outlet 6.2 is provided with a liquid container 6.3 and with a pump 6.4 delivering the liquid therefrom to the liquid inlet 6.1. The arrangement is such that the liquid inlet 6.1 is positioned above the liquid outlet 6.2 and preferably the entire inventive apparatus is vertically positioned. Thus, the liquid flows under gravity through the helical duct 6 and, under the action of the heater 8, evaporates in the passage 5 the particles entering and flowing through the same in order to form condensation nuclei.

Figure 3:
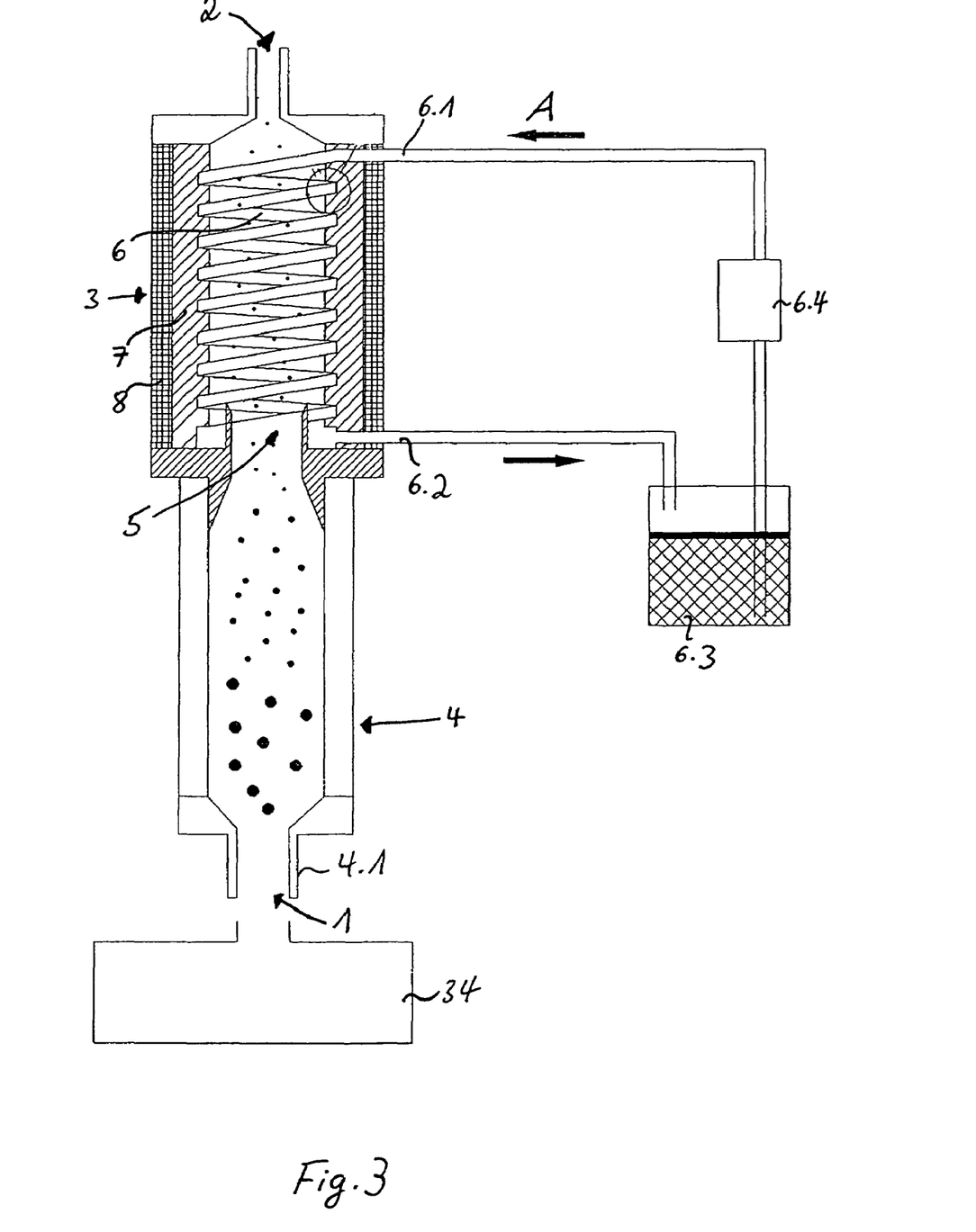
FIG. 3 An inventive apparatus for condensing steam on condensation nuclei with a connected particle counter.

In the apparatus for the condensation of steam on condensation nuclei shown in FIG. 3 a condensation flue 4 is connected to the passage 5. In passage 5 and in particular in condensation flue 4 there is a condensation of the steam produced in evaporating zone 3 on the condensation nuclei and on and with the same condensate particles of larger size are formed at outlet 4.1 than in the case of the condensation nuclei entering at inlet 2. The heating capacity and minimum pump delivery can be matched to one another so that the evaporating zone can have a 100% steam saturation. Unevaporated liquid flows back through the outlet 6.2 into the storage container 6.3. The particle size condensed on is dependent on the steam concentration.

Together with a particle counter 34 connected to the outlet 4.1, the apparatus according to the invention forms a condensation nucleus counter for counting aerosol particles functioning as condensation nuclei and which can in particular be smaller than can be detected as such by the particle counter 34. Thus, the entering aerosol particles are enlarged to form larger condensation particles by the condensation of evaporated liquid on the nuclei and they can then be detected and counted by the particle counter. The aerosol nuclei can be solid or liquid particles or droplets. They can be sucked from the ambient air or can be supplied to the inlet 2 from the outlet of an internal combustion engine, burner or the like, in order in this way to count the particle concentration in the gas or the air entering inlet 2.

The aerosol concentration differs and is to be measured. The heater is adapted to the material to be evaporated. The pump is set to a minimum delivery, so that there is a 100% saturation in the evaporating zone, independently of the temperature. The remaining, unevaporated material flows back into the storage container. The particle size changes with the aerosol concentration.

Figure 4:
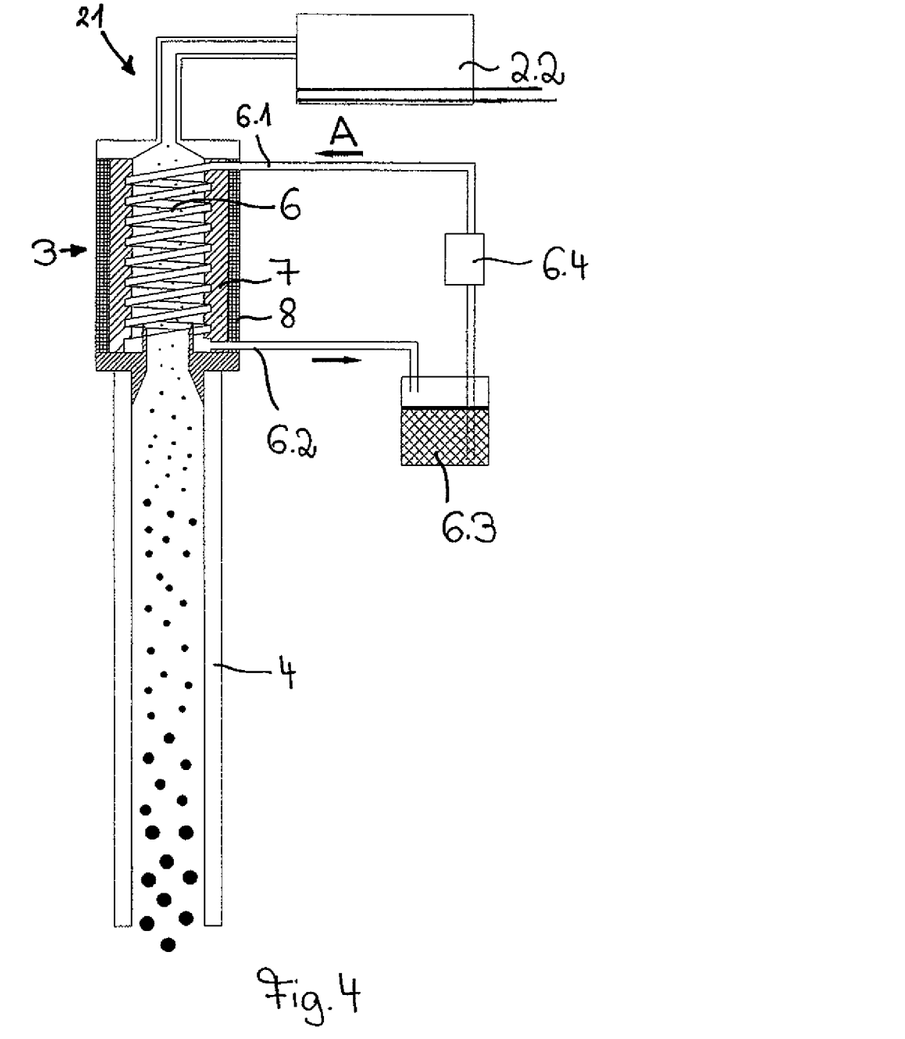
FIG. 4 An inventive apparatus in a single-stage arrangement as part of a monodisperse aerosol generator.

A second field of use of the inventive apparatus is in the calibration of aerosol spectrometer units. For this purpose an aerosol generator can be connected to the inlet 2 of the apparatus according to FIG. 1 and produces or generates condensation nuclei with a constant concentration (FIG. 4). The aerosol spectrometer unit is then connected to the outlet.

A single-stage, monodisperse aerosol generator is shown in FIG. 4. Identical parts are given the same reference numerals and for their description reference should be made to the description of FIGS. 1 and 3. The monodisperse aerosol generator 21 of FIG. 4 has a core source 22 for producing condensation nuclei, preferably with diameters below 100 nanometers and with a constant concentration. To the core source 22 is connected a device 1 in the form described relative to FIG. 1. The device 1 essentially comprises an evaporating zone 3 and condensation flue 4. To the latter is then connected the not shown aerosol spectrometer unit to be calibrated.

The aerosol concentration produced is constant and is determined by the rate of the condensation nuclei produced by the core source 22. The temperature of heater 8 is above the boiling point of the liquid to be evaporated. The size of the condensate particles is determined solely via the steam quantity and changes with the latter. Therefore the aerosol spectrometer unit can be calibrated over a wide particle size range which can be adjusted with the pump.

Figure 5:
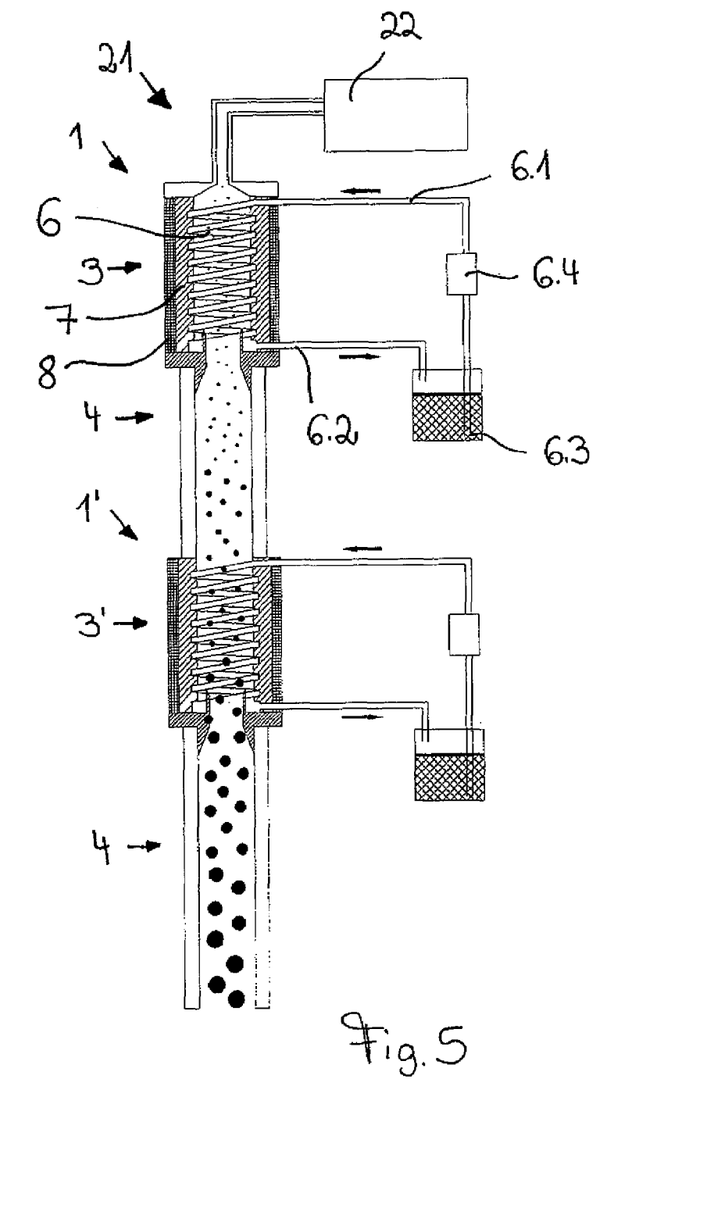
FIG. 5 An inventive apparatus in a cascaded arrangement as part of a monodisperse aerosol generator.

FIG. 5 shows a monodisperse aerosol generator in cascaded form with two evaporating devices according to the invention. To a first evaporating device 1 according to FIG. 1 is connected a second device 1', which is also constructed in the manner described relative to FIG. 1. This device also has an upstream core source 22. Otherwise what was stated regarding the single-stage construction of FIG. 4 applies.

In both constructions the aerosol concentration is constant and the particle size is controlled solely via the steam quantity. The heater temperature is above the boiling point of the material to be evaporated. The condensation flue is longer, because cooling takes place from higher temperatures. The particle size changes with the steam quantity.

Figure 6:
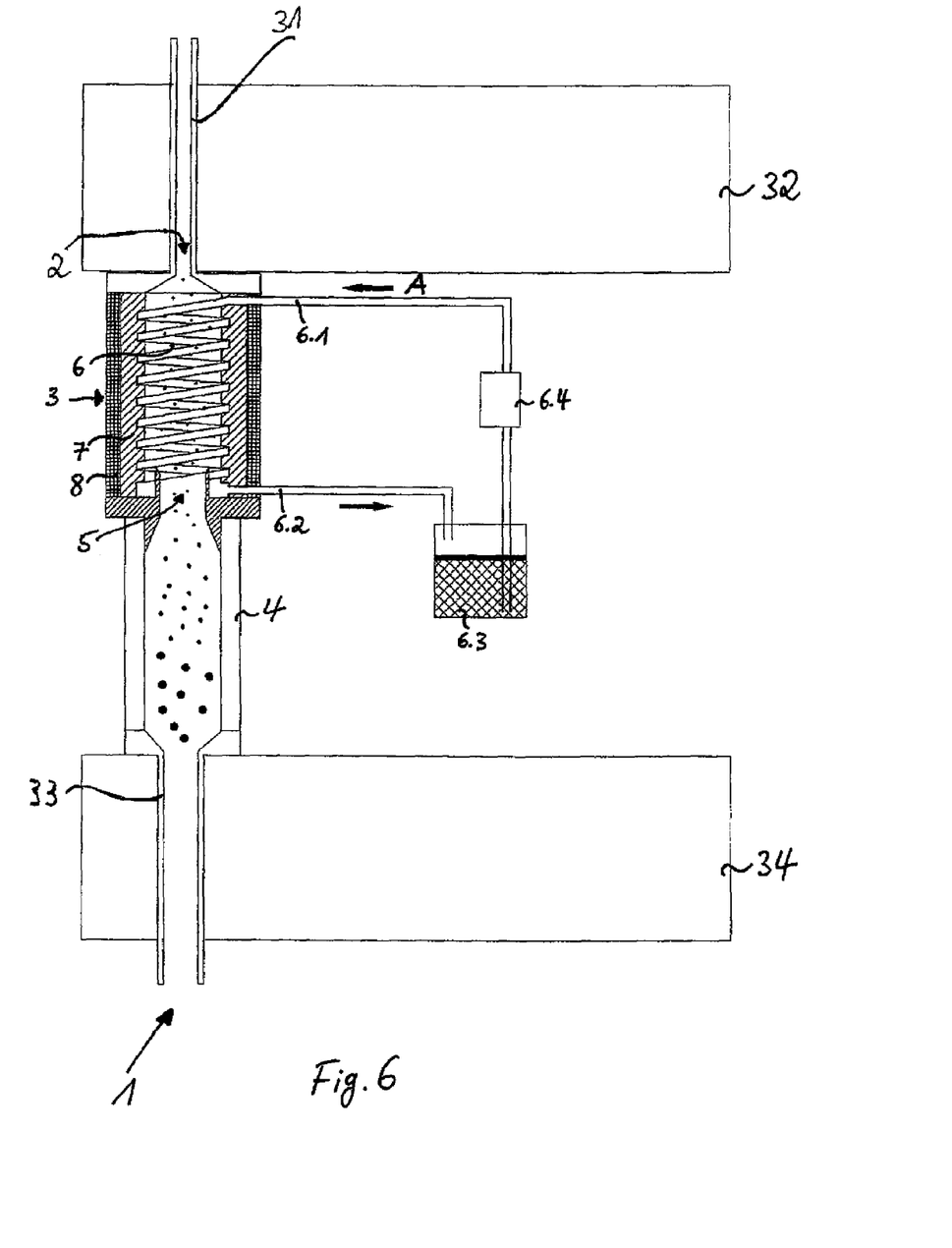
FIG. 6 An inventive apparatus for condensing steam on condensation nuclei with an additional aerosol spectrometer at the inlet and as a result of the subtraction of the selected results from the aerosol spectrometer results, it is possible to unambiguously determine the number of condensed on particles below the lower detection limit of the aerosol spectrometer.

FIG. 6 shows a particle measuring device with an inventive apparatus for condensing steam on condensation nuclei with which the total number of particles is detected and larger particles, such as those e.g. having a diameter above 0.3 æm are spectrometrically determined with respect to their size distribution, whilst additionally the proportion of smaller particles (below approximately 0.3 µm) can be detected.

For this purpose upstream of the inlet 2 of device 1 for condensing steam on condensation nuclei is provided an inlet tube 31 with which is associated a first aerosol spectrometer 32. The latter can be constructed in conventional manner and e.g. can have a construction, particularly with regards to its optical design, such as is described in EP 889 318 A1 and EP 1 331 475 A1.

To the aerosol spectrometer 32 is connected the inventive apparatus for condensing steam on condensation nuclei and such as has been described in particular relative to FIG. 1 and to which reference should be made. To the condensation flue is connected an outlet tube 33 with which is associated a further aerosol spectrometer 34.

The aerosol spectrometer 32 detects the aerosol entering through the inlet tube 31, such as from ambient air, exhaust gases of an internal combustion engine, or a burner, etc. with respect to the concentration and size distribution for entering particles larger than approximately 0.3 µm. All the particles, including the smaller particles, form condensation nuclei for condensing steam in the corresponding apparatus 1. As a result of the condensation aerosol particles smaller than 0.3 µm also evolve to condensate particles having a size exceeding this value and consequently their number can be detected by the aerosol spectrometer 34 enabling the detection of the total particle concentration in the entering particle flow. A size determination by the aerosol spectrometer 34 would obviously be pointless here, because the particles passing through the outlet duct 33 are enlarged by the condensed on liquid and consequently the true particle size cannot be established. In place of the aerosol spectrometer 34 it is also possible to use a conventional particle counter. From the difference of the particle concentrations detected by the aerosol spectrometer 34 (or a particle counter) and the aerosol spectrometer 32, it is also possible to establish the concentration of particles below 0.3 µm in the inlet flow.

REFERENCE NUMERALS LIST

1/1' Device
2 Inlet
3 Evaporating zone
4 Condensation flue
4.1 Outlet
5 Passage
6 Duct
6a Bottom
6b Side
6c/6d Wall
6.1 Duct inlet
6.2 Duct outlet
6.3 Liquid container 6.4 Pump
7 Wall
8 Heater
11 Particle counter
21 Aerosol generator
22 Core source
31 Inlet tube
32/34 Aerosol spectrometer

The invention claimed is:

1. Apparatus for producing a monodisperse aerosol with an aerosol generator, wherein the aerosol generator is followed by at least one apparatus for condensing steam on condensation nuclei comprising a device for humidifying gas with an inlet and an evaporating zone for liquid, wherein a flow area has a heated liquid duct open thereto, and a condensation flue connected to the flow area.

2. Apparatus according to claim 1, wherein a condensate particle size is variable and adjustable by modifying a steam quantity.

3. Apparatus according to claim 1, wherein the aerosol generator is followed by at least two of said apparatus for considering steam on condensation nuclei arranged in series.

4. Device for humidifying gas with an inlet and an evaporating zone for a liquid, wherein a flow area has a heated liquid duct open thereto, and wherein the liquid duct is arranged around the flow area in the form of a helical channel.

5. Device according to claim 4, wherein an inlet in the flow area is positioned on the top of the flow area.

6. Device according to claim 4, wherein the flow area is vertically oriented.

7. Device according to claim 4, wherein the liquid inlet in the liquid duct is positioned above an outlet for unevaporated residual liquid.

8. Device according to claim 4, wherein a liquid container and a pump are positioned upstream of the inlet for the liquid to be evaporated in the flow area.

9. Device according to claim 8, wherein a line leads to the container from the outlet for the unevaporated residual liquid.

10. Apparatus for condensing steam on condensation nuclei, wherein a device for evaporating gas according to claim 4 and a condensation flue connected to the flow area are provided.

11. Apparatus according to claim 10, wherein the condensation flue is vertically oriented and/or is positioned below the flow area.

12. Apparatus for counting particles with a particle counter or an aerosol spectrometer, wherein upstream of the particle counter or aerosol spectrometer is provided an apparatus according to claim 10.

13. Apparatus for counting small diameter particles with at least one particle counter, wherein a first particle counter is followed by an apparatus according to claim 10 and in turn the apparatus for condensing steam in condensation nuclei is followed by a further particle counter.

14. Apparatus according to claim 13, wherein the at least one particle counter is in the form of an aerosol spectrometer.

15. Apparatus according to claim 10, wherein an inlet in the flow area is positioned on the top of the flow area.

16. Apparatus according to claim 10, wherein the flow area is vertically oriented.

17. Apparatus according to claim 10, wherein the liquid inlet in the liquid duct is positioned above an outlet for unevaporated residual liquid.

18. Apparatus according to claim 10, wherein a liquid container and a pump are positioned upstream of the inlet for the liquid to be evaporated in the flow area.

19. Apparatus according to claim 18, wherein a line leads to the container from the outlet for the unevaporated residual liquid.

20. Apparatus according to claim 12, wherein an inlet in the flow area is positioned on the top of the flow area.

21. Apparatus according to claim 12, wherein the flow area is vertically oriented.

22. Apparatus according to claim 12, wherein the liquid inlet in the liquid duct is positioned above an outlet for unevaporated residual liquid.

23. Apparatus according to claim 12, wherein a liquid container and a pump are positioned upstream of the inlet for the liquid to be evaporated in the flow area.

24. Apparatus according to claim 23, wherein a line leads to the container from the outlet for the unevaporated residual liquid.

25. Apparatus according to claim 13, wherein an inlet in the flow area is positioned on the top of the flow area.

26. Apparatus according to claim 13, wherein the flow area is vertically oriented.

27. Apparatus according to claim 13, wherein the liquid inlet in the liquid duct is positioned above an outlet for unevaporated residual liquid.

28. Apparatus according to claim 13, wherein a liquid container and a pump are positioned upstream of the inlet for the liquid to be evaporated in the flow area.

29. Apparatus according to claim 28, wherein a line leads to the container from the outlet for the unevaporated residual liquid.

* * * * *